United States Patent [19]  
Vary et al.

[11] Patent Number: 4,767,699  
[45] Date of Patent: Aug. 30, 1988

[54] DIAGNOSTIC REAGENT, KIT AND METHOD EMPLOYING POLYNUCLEOTIDE DISPLACEMENT, SEPARATION, ENZYMATIC CLEAVAGE AND ADENOSINE PHOSPHATE DETECTION

[75] Inventors: Calvin P. H. Vary, Califon; Steven E. Diamond, Springfield, both of N.J.; Neil M. Wolfman, Brookline, Mass.

[73] Assignee: Allied Corporation, Morristown, N.J.

[21] Appl. No.: 729,503

[22] Filed: May 2, 1985

[51] Int. Cl.$^4$ .................... C12Q 1/68; G01N 33/53; G01N 33/566

[52] U.S. Cl. ............................. 435/6; 435/7; 435/810; 436/501; 436/808; 536/26; 536/27; 536/28; 935/77; 935/78

[58] Field of Search .................. 435/6, 7, 810, 77, 78; 436/501, 808; 536/26

[56] References Cited  
U.S. PATENT DOCUMENTS 3,423,290 1/1969 Seamans .  
3,933,592 1/1976 Clendenning .  
4,205,952 6/1980 Cais ..................... 436/518  
4,235,961 11/1980 Lundin .  
4,246,340 1/1981 Lundin et al. .  
4,286,057 4/1981 Wulff et al. .  
4,358,535 11/1982 Falkow et al. .  
4,446,231 5/1984 Self .

FOREIGN PATENT DOCUMENTS 0063879 4/1982 European Pat. Off. .  
0070687 7/1982 European Pat. Off. .  
0097373 6/1983 European Pat. Off. .  
0124221 3/1984 European Pat. Off. .  
8403520 9/1984 PCT Int'l Appl. .  
2139349 11/1984 United Kingdom .

OTHER PUBLICATIONS

Wu, M. et al., Proc. Natl. Acad. Sci., 78, No. 11: 7059–7063 (1981).  
Molloy, G. R. et al., Biochem, 11, No. 17: 3256–3260, (1972).  
Sorez, H. et al., Jour. Mol. Biol., 88: 233–245 (1974).  
Holm-Hansen, O. et al., Methods in Enzymology, vol. LVII: pp. 73–85 (1978).  
Dunn., A. R. et al., Methods in Enzymology, vol. 65: pp. 468–478 (1980).  
U. S. Littauer et al., "Polynucleotide Phosphorylase" The Enzymes, vol. XV, pp. 517–553 (1982).  
C. A. Saunders et al., "Preparation of Ribomopolymers of Defined Length" Analytical Biochemistry 95, pp. 171–173 (1979).  
W. D. McElroy et al., J. Appl. Biochem., vol. 5, pp. 197–209 (1983).  
F. R. Leach, J. Appl. Biochem., vol. 3, pp. 473–517 (1981).

Primary Examiner—Robert J. Warden  
Assistant Examiner—Jack Spiegel  
Attorney, Agent, or Firm—Alan M. Doernberg

[57] ABSTRACT

A reagent complex is disclosed containing (1) a probe polynucleotide having a target binding region complementary to a target nucleotide sequence and (2) a signal strand polynucleotide bound by base pairing to a portion of the target binding region. The signal strand is displaced from the reagent complex by the target nucleotide sequence and separated from intact reagent complexes. A digestable ribonucleotide segment of the displaced signal strand, such as a 3' terminal segment, is digested to ribonucleotide phosphates, which are phosphorylated to ATP. The ribonucleotide phosphates or ATP are detected.

27 Claims, 2 Drawing Sheets

DIAGNOSTIC REAGENT, KIT AND METHOD EMPLOYING POLYNUCLEOTIDE DISPLACEMENT, SEPARATION, ENZYMATIC CLEAVAGE AND ADENOSINE PHOSPHATE DETECTION

BACKGROUND OF THE INVENTION

The present invention relates to a diagnostic assay method, reagent and kit for detecting the presence of a DNA target nucleotide sequence in a biological sample.

Conventional methods for detecting the presence of a particular polynucleotide in a biological sample typically involve immobilization of nucleic acid of the sample on a surface as the initial step. Once the sample is immobilized, a probe polynucleotide strand, usually tagged with a detectable label such as radioactive phosphorus atoms, is incubated with the immobilized sample so as to bind to the immobilized sample by purine/pyrimidine base sequence-specific complementary base pairing when the immobilized sample contains the target nucleotide sequence. After washing off the labeled probe which has not so hybridized, the presence or absence of label on the support is then determined. Techniques for this determination include exposure of a photographic film, liquid scintillation counting, and fluorescence microscopy. See U.S. Pat. No. 4,358,535 to Falkow et al. (1982).

Ward and coworkers (see EPA No. 63,879 (1982)) have described a variation of this technique in which, rather than tagging the probe directly with a detectable label, the probe is tagged with a nonisotopic substituent such as biotin on certain nucleotides. In such cases, after the unhybridized probe is washed off, the support is contacted with a reagent such a avidin linked to an enzyme. The avidin-enzyme complex binds selectively to biotin because of the high avidin-biotin binding affinity, so as to affix enzyme selectively where the target nucleotide sequence has been immobilized on the support. Thereafter, a substrate for the enzyme is added and products of the enzymatic reaction are detected, yielding an amplified signal functionally dependent upon the initial concentration of target nucleotide sequence on the support. See also EPA No. 97,373 of ENZO BIOCHEM, INC (Jan. 4, 1984).

A variation in the above nonisotopic system has also been described in another European patent application of Standard Oil of Illinois (EPA No. 70,687 (1983)) in which, in one form (see pages 8-10 thereof), two nucleic acid probes specific for the target nucleotide sequence are employed. The first probe, which can hybridize to a first portion of the target nucleotide sequence, is affixed to a solid support such that, upon incubation of the solid support with a sample of the biological material, target nucleotide sequences in the sample will bind to the support selectively via this first immobilized probe. Thereafter or concurrently, the second probe, which can hybridize selectively to a second and distinct portion of the target nucleotide sequence, is exposed to the support. Again, if the target nucleotide sequence is present in the biological sample, the second probe will bind selectively to that nucleotide sequence; and a combination structure (or sandwich) will be created linking the second probe to the support via the first probe and the target nucleotide sequence. The published patent application discloses labeling this second probe with a moiety directly or indirectly generating or absorbing specific wavelengths of light (e.g., a fluorescent label, a phosphorescent label or a chemiluminescent label). By separating the support from unbound solution constituents at each stage, the presence of label in the phase with support after the third separation will be a function of the presence and concentration of the target nucleotide sequence in the sample.

While the above hybridization procedures will detect the presence of target nucleotide sequences in biological samples in many cases, they each have the disadvantage of either multiple steps or steps with necessarily long incubation periods that make them impracticable for easy use in a clinical laboratory. Furthermore, many of these processes suffer from a limited selectivity or sensitivity with regard to interfering polynucleotide sequences or reliable detection of low levels of target nucleotide sequence against the background signal. In particular, nonspecific binding of the labeled probe represents a substantial source of background signal in each process.

Various assays for ATP in biological samples have been proposed, based primarily upon a bioluminescence reaction wherein the enzyme luciferase causes the generation of detectable light from luciferin (provided in excess) and ATP (the analyte). Review articles include W. D. McElroy et al., *J. Appl. Biochem*, vol. 5, pp. 197-209 (1983) and F. R. Leach, *J. Appl. Biochem.*, vol. 3, pp. 473-517 (1981); U.S. patents include 3,933,592 to Clendenning et al. (1976). Applicants are unaware of any disclosed use of this reaction in nucleic acid assays other than page 6, lines 26-30, and page 8, lines 6-13, of EPA No. 70,687 (1983), wherein luciferase is the tag.

Other assays for riboadenosine phosphate are described in U.S. Pat. No. 4,446,231 to Self (1984), involving in some cases, an amplified change in a molecule such as NADH detectable by absorbance or fluorescence.

Displacement geometries for nucleic acid assays are described in the following pending U.S. applications assigned to Allied Corporation and Genetics Institute, Inc.:

| U.S. Ser. No. | Filed | Inventors |
| --- | --- | --- |
| 607,885 | May 7, 1984 | S. E. Diamond et al. |
| 684,305 | December 20, 1984 | M. Collins et al. |
| 684,308 | December 20, 1984 | J. I. Williams et al. |

No reference to the particular types of detection systems described herein are contained in those three applications.

BRIEF DESCRIPTION OF THE INVENTION

The present invention provides a method for determining the presence of a predetermined DNA target nucleotide sequence in the nucleic acid of a biological sample which comprises the steps:

(a) providing a reagent complex of (i) a probe polynucleotide which is capable of base pair binding via hydrogen bonds of purine/pyrimidine bases to the target nucleotide sequence, and (ii) signal strand polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the target nucleotide sequence, the signal strand polynucleotide containing cleavable riboadenosine nucleotides;

(b) contacting the reagent complex with a sample under conditions in which the target nucleotide sequence, if present, binds to the probe polynucleotide and displaces signal strand polynucleotide from the complex;

(c) separating a first phase containing displaced signal strand polynucleotide from a second phase containing reagent complexes;

(d) digesting the displaced signal strand polynucleotides in the first phase to produce ribonucleoside phosphates; and (e) detecting the riboadenosine phosphate monomers in the ribonucleoside phosphates.

Preferably, the riboadenosine phosphate monomers are ADP, and the detection includes phosphorylation to ATP, e.g., with phosphoenol pyruvate and pyruvate kinase. The resultant ATP can be detected e.g., by bioluminescence. Alternatively, the byproduct pyruvic acid can be detected, e.g., by reaction with NADH in the presence of lactate dehydrogenase, with the disappearance of NADH monitored photometrically.

The present invention also provides a reagent complex, as described above.

The present invention also provides a diagnostic kit for determining the presence of a predetermined target nucleotide sequence in the nucleic acid of a biological sample comprising:

(a) a reagent complex comprising:
  (i) a probe polynucleotide containing a target binding region capable of complementary base pair binding to the target nucleotide sequence, and
  (ii) a signal strand polynucleotide bound by complementary base pairing to a portion of the target binding region, the signal strand polynucleotide containing a plurality of cleavable adenosine ribonucleotides;
  the target nucleotide sequence being capable of displacing the signal strand polynucleotide from the reagent complex;

(b) separation means for separating displaced signal strand polynucleotides from reagent complexes;

(c) enzymatic means for cleaving separated displaced signal strand polynucleotides and producing riboadenosine phosphate monomers; and (d) detecting means for detecting riboadenosine phosphate monomers produced by the enzymatic means.

The present invention further provides the reagent complex used in such a method. The present invention further provides a detectably labeled polynucleotide containing a pairing segment of DNA complementary to or homologous to a target nucleotide sequence to be detected and, at its 3' end, a ribonucleotide segment containing adenosines.

DETAILED DESCRIPTION OF THE INVENTION

In this application the following terms are used based on their generally accepted meanings in the field of molecular biology:

Polynucleotide or Polynucleotide Strand refers to a linear polymeric structure of pentose sugars (generally ribose or deoxyribose) linked to each other by 3', 5'-phosphodiester linkages, and linked by carbon-nitrogen bonds at the 1-carbon of the sugar to pendant purine or pyrimidine bases such as, but not limited to uracil (linked naturally to ribose only as rU), thymine (linked naturally to deoxyribose only as dT), cytosine (as in dC or rC), adenine (as in dA or rA) and guanine (as in dG or rG). Polynucleotides thus include strands of deoxyribonucleic acid (DNA) and strands or ribonucleic acid (RNA) or continuous heteropolymers of both types of polynucleotides.

The ends of such Polynucleotide Strands are referred to as the Five Prime (5') ends, where the 5-carbon of the pentose is not linked to another pentose (but may bear hydroxyl, monophosphate or other natural or synthetic moieties), or the Three Prime (3') ends, where the 3-carbon of the pentose is not linked to another pentose (but may similarly bear hydroxyl, monophosphate or other natural or synthetic moieties).

Complementary Base Pairing or Purine/Pyrimidine Base Pairing refers to the hydrogen bonding between opposite bases pendant on two antiparallel Polynucleotide Strands, which is most energetically favorable for natural DNA when dG is opposite dC and dA is opposite dT. Bases other than the five naturally-prevalent ones also have preferential pairing: for example, 5-methylcytosine binds preferentially to guanine. For illustrative purposes, this pairing is shown in many of the Figures by parallel straight lines with complementary strands directed in antiparallel directions (in the 5' to 3' sense). It should be appreciated, however, that the actual geometry of double-stranded segments will normally be helical (the well-known double helix) of various pitches, as schematically illustrated in FIG. 1D.

Hybridization is used herein to refer to admixing two Polynucleotides under conditions conducive to the formation of double-stranded structures, with Complementary Base Pairing causing such double stranded structures to form where complementary sequences or nearly complementary sequences are present.

The basic components of the method of the invention are a probe polynucleotide (sometimes called herein the probe), a signal strand polynucleotide (sometimes called herein labeled polynucleotide), various enzymes and the biological sample containing nucleic acid, a portion of which is sometimes called herein the target polynucleotide or target nucleotide sequence. A sample may or may not contain a target nucleotide sequence. In some cases a support is also provided, either to which the reagent complex is immobilized via the probe (such that the probe is sometimes called an immobilized probe or immobilized probe polynucleotide), or in other cases as a part of the separation step that follows displacement. In practicing the method, additional reagents or equipment are required for readout; the term readout refers to the indirect detection of signal strand polynucleotide in one or more phases of (separated) reaction materials, and especially in a liquid phase by virtue of displacement from the reagent complex and separation of displaced signal strand polynucleotide in solution from probe polynucleotides and reagent complexes.

In the practice of the present invention, the probe polynucleotide can be a linear or circular polynucleotide capable of binding specifically through complementary base pairing in at least one region of its purine/pyrimidine base sequence to specific target nucleotide sequences of a sample. This binding may be between DNA and RNA or between DNA and DNA. Accordingly, the probe may either be DNA or RNA. As discussed more fully below, it is generally only a specific region of the probe which binds selectively to the target nucleotide sequence. Other regions of the probe may be of various naturally occurring or synthesized sequences which do not participate in the hybridization reaction with the target nucleotide sequence, but which may play an important role in the present invention, e.g., by serving as a site for attachment to a support or by providing some degree of separation between the support and the region to which the target nucleotide sequence binds, if desired.

The probe polynucleotide (probe) used in the method, reagent complex and kit of the present invention can be of any type described in U.S. Ser. Nos. 607,885, 684,305 and 684,308 with four additional preferences.

The probe polynucleotide is preferably DNA, but may also be RNA. It is preferred that the sample be rendered free of endogeneous RNA, nucleoside triphosphates, nucleoside diphosphates and (in some cases) nucleoside monophosphates before the contacting step. The probe preferably does not contain long (over 10 bases) homopolymeric segments of U or T. The former preferences are to avoid riboadenosine phosphates of probe or sample origin; the latter preference is to avoid non-specific binding of the poly A tail of the signal strand polynucleotide to such homopolymeric segments of the probe during manufacture or use of the reagent complex.

Referring to the region of the probe to which the target nucleotide sequence will specifically bind, called herein the target binding region (TBR in the Figures), the binding may be (and preferably is) perfect, in the sense that each nucleotide in the sequence finds its correct complementary binding partner (e.g., dA to dT) in the target nucleotide sequence, or may contain some mismatches. At least one portion of the target binding region of the probe is preferably single-stranded in the reagent complex, i.e., it is not complementary to signal strand polynucleotide sequences nor self-complementary; this single-stranded region is sometimes called herein the initial binding region (IBR in the Figures) because the target nucleotide sequence can bind to this region of bases without displacing any of the signal strand polynucleotide. Such initial binding region of the probe is at least fifteen bases in length, and is preferably at least fifty bases in length. The overall target binding region includes the initial binding region and most or (preferably) all of the signal-strand polynucleotide binding region (LBR in the Figures and in the discussion below). The length of the overall target binding region is not independently critical, but rather can be considered as a function or sum of the preferred or more preferred lengths of the IBR and LBR portions. Base lengths of the initial binding region of the probe above five hundred are generally not required, but are not significantly disadvantageous in most cases. A suitable lower limit on the length of this region of base pairing for clinical laboratory applications is somewhat dependent upon base sequence of the target binding region of the probe polynucleotide and base composition and other physical factors described below, and especially upon the conditions for intended hybridization, mode of attachment, if any, of the probe to a support, kinetics of hybridization and the readout system employed.

The solid phase to or on which the probe can be immobilized in certain embodiments may be of almost any conventional type, including especially polymeric materials, ceramic materials, walls of a test tube or other container, paper, nitrocellulose or glass. In some forms of the invention, the solid phase consists of natural, modified natural or synthetic particles or beads made of materials such as protein, fixed cells or viruses or of various polymers such as polystyrene, latex or glass.

The means of attachment of the probe to the solid support in certain embodiments of the invention may be simple adsorption, but is preferably some form of specific covalent, linkage, ionic bonding, hydrophobic interaction or hydrogen bonding. In the case of covalent linkage, the binding may be direct as by reaction between chemical moieties on the surface of the support (for example, amine or carboxyl moieties) and moieties on the polynucleotide, and especially hydroxyl or phosphate moieties on the end sugar rings of the polynucleotide. Linking agents which are specific to the free secondary hydroxyl normally present at the 3' end include phosphites, succinic anhydride and phthalamide. Linking agents which are specific to the phosphate normally present on the sugar at the 5' end (at least for most naturally occurring polynucleotides or products or most cleavage reactions) include carbodiimides such as 1-ethyl-3,3-dimethylaminopropylcarbodiimide, with or without imidazole or 1-methylimidazole. See B. C. F. Chu et al., *Nucleic Acids Research* Vol. 11, No. 8, pp. 6513-29 (1983). Such linkages which are specific to an end or other small portion of the probe, if remote from the target binding region, may permit greater degrees of freedom during the hybridization reaction compared to adsorption or other similar physical or non-specific chemical means of attachment. With such greater degrees of freedom, the minimum length of the target binding region or minimum time for the hybridization to progress to a detectable level may be lowered.

Non-specific covalent linkages include linkages between the substrate and free bases along the chain via moieties such as m-aminobenzyloxy methyl (ABM), m-diazobenzyloxy methyl (DBM) or o-aminophenylthioether (APT). See H. Bunemann et al., *Nucleic Acids Research* Vol. 10, No. 22, pp 7163-7196 (1982) (two articles). Other exemplary non-specific linking chemistry is described in U.S. Pat. No. 4,286,964 to B. Seed (1981).

In addition to direct covalent linkage, the probe polynucleotide may be indirectly linked in a covalent fashion to the support by a linking or spacer molecule. Examples of indirect covalent linking reagents include spacer reagents which can react both with functional groups (for example, activated esters) on the support and by carbodiimide chemistries with the phosphate normally present on the 5' terminal sugar of the polynucleotide. Such spacer molecules include the aliphatic diamines used in the above-cited Chu et al. article which, once attached to the terminal phosphate, can then be linked to active groups on the support such as N-hydroxysuccinimide esters. Still other spacer molecules can also contain a functional moiety such as phenyl ketone which will react directly with a support having hydrazine moieties, forming a resultant hydrazone.

The probe further may be noncovalently linked to the support by interaction of some portion of the probe with affinity reagents that are adsorbed or covalently bound to the support. Examples include (1) immobilization on the support of a short single-stranded polynucleotide which can hybridize to some portion of the probe polynucleotide not overlapping with the region in the probe which is capable of binding to the target nucleotide sequence and (2) binding of a chemically modified probe polynucleotide carrying one or more avidin or biotin moieties to a support having biotin or avidin moieties, respectively, adsorbed or covalently bound to the support. The latter method is based on the high affinity ($K_{diss}$ approximately $10^{-15}$M) of the small molecule biotin for the protein avidin (or streptavidin).

While the present invention is not limited with regard to the spacings between the point or points of attachment of the probe to a support and the region of the probe polynucleotide which binds specfically to the target nucleotide sequence, it is preferable that this spacing be sufficiently large for the hybridization between target nucleotide sequence and target binding region of the probe polynucleotide to occur such that the target binding region of the probe has sufficient and preferably maximal obtainable freedom of movement during hybridization.

In other embodiments of the invention, the probe polynucleotide is not immobilized on a support, but rather the entire reagent complex is in solution as the reagent is mixed with a biological sample such that hybridization will occur, if at all, in solution. In some of those solution hybridization embodiments, the probe does contain a substituent (such as an affinity reagent, e.g., biotin, or a chemical moiety, e.g., a hapten such as nitrophenol) so as to be immobilizable or separable after hybridization, e.g., by passing through a porous bed or filter with strepavidin bound to a support matrix. Such immobilization will cause only displaced labeled polynucleotides to remain in the liquid phase, for subsequent determination. Still other forms of the invention involving solution hybridization include alternative methods of separations such as size exclusion chromatography, electrophoresis or other physical separation techniques.

Such probe polynucleotides can be manufactured reproducibly in a variety of ways, e.g., cloned in or as a part of a suitable plasmid or viral vector isolated from a bacterium or other suitable microorganism, as a part of the genetic material of a microbe or obtained from any other pertinent biological source. Generally, only a small region of nucleic acid that includes a probe polynucleotide sequence (a portion of which forms the target binding region) will be inserted into any such cloning vectors by recombinant techniques; the remainder, if any, of the cloned insert that is not probe polynucleotide sequence can be conveniently chosen from any polynucleotide sequence heterologous to the target nucleotide sequence. In certain embodiments of this invention, such heterologous sequences can include sequences deliberately selected for specific properties such as the presence of a unique restriction enzyme recognition site. Under some conditions an entire gene or a sequence including an entire gene may be used as an insert, with the vector plus inserted nucleotide sequence either in a circular or linear form. In the event that the probe polynucleotide is double-stranded when manufactured, denaturation (either thermally, by adjustment of pH or by disruption of base pairing with other conventional techniques) will normally follow isolation. Cleavage (especially by restriction enzymes or by site-specific chemical cleavage) will normally be used to form double-stranded segments or desired linear form and, if double-stranded circular forms are grown, will precede denaturation. In some cases it may be preferred to purify individual strands from a double-stranded structure either to be used individually as probe polynucleotides or with one as a probe polynucleotide and the other as a precursor for at least a portion of the signal strand. This purification can be done by standard techniques such as denaturing gel electrophoresis or affinity chromatography. In some instances, the probe polynucleotide is produced as a single-stranded molecule by replication using single-stranded vectors such as M13 bacteriophage.

Other aspects of the probe are incorporated herein by reference from the above-referenced U.S. Ser. Nos. 607,885, 684,305 and 684,308.

The signal strand polynucleotide of the present invention contains a pairing region bound, in the reagent complex, to the signal-strand polynucleotide binding region (LBR) of the probe polynucleotide. The pairing region is typically DNA, but it may also be RNA. The signal strand polynucleotide also contains (usually at its 3' end) a polyribonucleotide portion (separate from the pairing region when the pairing region is DNA, optionally including the pairing region when the pairing region is RNA). Preparation of DNA/RNA constructs for this purpose is described below after the complete description of the method of use. In many forms of the invention, the polyribonucleotide segment is either homopolymeric poly A or an A-rich heteropolymeric ribonucleotide sequence. The polyribonucleotide sequence may be as short as 2 nucleotides, but is typically at least 100, preferably at least 1000 and more preferably at least 5000 nucleotides in length. The number of adenosines in the polyribonucleotide segment provides a degree of amplification between the displacement step (contacting step (b)) and detecting step (e) of the method of the present invention.

For a sample to be analyzed according to the present invention, sample is concentrated and treated to convert such DNA into detectable form. It is first desirable to release the DNA from structures (cells, viruses) by sonication, extractions or other physical or chemical treatments, and then to concentrate the nucleic acid fraction. In some forms of the invention, the sample DNA may be cut randomly or at specified locations (e.g., by restriction enzymes) and/or denatured. Exemplarly treatments include denaturation with sodium dodecyl sulfate (SDS) or guanidinium thiocyanate, strong alkali treatment, proteolysis, RNAse treatment, phenol extraction or some combination of these. For the present invention, it is desirable to remove endogenous RNA, and may be desirable to remove endogenous ADP and ATP (and in some forms of the invention endogenous AMP). Endogenous RNA can be removed by alkaline conditions (e.g., NaOH), which also denatures the double-stranded DNA. Endogenous ATP, ADP and AMP can be consumed enzymatically (e.g., with phosphatases which are inactivated and/or removed after this step) if desired. As described below, however, once endogenous RNA is removed, one can, in some forms of the invention, deal with endogenous ATP, ADP and (in some forms) AMP as a known background value (and then deal with them mathematically), rather than to use chemical, biochemical or physical methods, as in other forms of the invention.

The conditions for the displacement step (contacting step (b)) of the method of the present invention are (subject to the above constraints) generally those disclosed in U.S. Ser. Nos. 607,885, 684,305 and 684,308. Higher temperatures during this step (e.g., 45°–80° C.) are not disadvantageous to the present invention (provided that the pairing region is sufficiently long to prevent non-specific dissociation) since the label or tag (the polyribonucleotide segment) is substantially temperature-insensitive. Additives are preferably avoided, however, which will interfere with the subsequent digesting step (d) or the phosphorylating step (e)(ii) also found in many read-outs (e.g., the actions of polynucleotide phosphorylase (or of phosphodiesterase and myokinase), of pyruvate kinase and of luciferase, respectively). Generally satisfactory conditions include moderate (0.2-0.5M) salt concentrations, pH 6-8 and temperatures of 15°-90° C. As indicated in application U.S. Ser. No. 684,305, lower temperatures (e.g., 25°-45° C.) and moderate pH (e.g., near pH 7.5) are preferred when a recombination protein (e.g., rec A protein from *E. coli*) is present. As indicated in U.S. Ser. No. 607,885, optimal temperature may be affected by lengths of bonding in the reagent complex (especially if under about 100 nucleotide pairs).

The separating step (c) of the present method may be of various types depending upon whether or not the probe is immobilized in the reagent complex or contains an immobilizable group (e.g., biotin or a homopolymeric tail). For immobilized reagent complexes, the separation step can include removing some or all of the liquid phase containing displaced signal strand polynucleotide from the solid phase. Either purely physical separation, decantation, filtration or magnetic attraction of magnetically-attractable solid supports (e.g., iron-filled beads) can be employed.

When the probe contains an immobilizable group, the separation step (c) can include passing the product solution of the displacement step (contacting step (b)) in intimate contact with an immobilized affinity reagent for the immobilizable group (e.g., strepavidin or avidin for biotin on the probe). The form of such separation used in present Example 1 involves the affinity of immobilized oligo-dG for the poly-dC, tail on the probes as described in more detail in U.S. Ser. No. 729,501 of P. D. Unger et al., filed May 2, 1983.

When the probe neither is immobilized nor contains an immobilizable group, other means of separation may be employed. These include electrophoresis, HPLC, hydroxylapatite chromatography and other double-strand specific reagents such as DNA binding proteins or netropsin affinity columns.

Once the liquid phase has been obtained containing displaced signal strand polynucleotide, the signal strand polyribonucleotide segment is digested. In preferred forms of the invention, enzymatic means are used for this digesting step which digest processively (staying attached to the polynucleotide starting at the 3′ hydroxy end and releasing sucessively individual ribonucleotide phosphates).

In some preferred forms, such enzymatic means produce ribonucleoside diphosphates (adenosine 5′-diphosphate or ADP in the case of poly A as the polyribonucleotide segment; mixtures of ADP, GDP, CDP and UDP in the case of heterogeneous polyribonucleotide segments). Exemplary enzymes producing ribonucleoside diphosphates are the primer dependent polynucleotide phosphorylases (also called polyribnucleotide phosphorylases or PNP), sch as those derived from *E. coli* and from *Micrococcus leuteus*. See *The Enzymes*, vol. XV, Part B, pp. 518-556 (Academic Press; P. D. Boyer, ed., 1983). In other preferred forms of the invention, such enzymatic means produce ribonucleotide monophosphates (AMP in the case of polyA as the polyribonucleotide segment; mixtures of AMP, GMP, CMP and UMP in the case of heterogenous polyribonucleotide segments). Exemplary such enzymatic means producing ribonucleotide monophosphates include snake venom phosphodiesterase. Less preferred are the nonprocessive enzymes that produce ribonucleotide oligomers (e.g., pancreatic RNase).

Conditions for the digesting step are, in general, chosen for efficient enzymatic activity in the desired direction (many of the enzymes used are capable of catalyzing the reverse reaction whereby ribonucleotides are added to the 3′ end of the polyribonucleotide segment). For polynucleotide phosphorylase, the release of the first nucleotide can be illustrated as follows:

$$DNA\text{-}(rA)_n + Pi \rightleftharpoons DNA\text{-}(RA)_{n-1} + ADP$$

In addition to the normal conditions and cofactors for the enzyme (e.g., pH 8-9, magnesium ion, 2-mercaptoethanol), the forward reaction desired during the digestion step is helped by excess inorganic phosphate (supplied in Example 1 as sodium phosphate). The forward reaction can, under certain circumstances, be inhibited by an accummulation of ADP (or in certain cases, other nucleoside disphosphates). This inhibition can generally be overcome either by dilution (large reaction volumes relative to the amounts of ADP anticipated) or by coupling the digestion step to the phosphorylation step (as described below and in a copending, commonly assigned application of Calvin Vary et al. entitled, "Method and Kit For Detecting Polyriboadenosine Segments and Messenger RNA," U.S. Ser. No. 729,502, filed May 2, 1985).

When a phosphodiesterase (or most other enzymes producing AMP) is used, the digestion step is substantially irreversible. Accordingly, the coupling desired is between the two phosphorylation steps (e.g., with myokinase and pyruvate kinase) rather than necessarily between the digestion step and the first phosphorylation step. The digestion step may be written:

$$DNA\text{-}(rA)_n \rightleftharpoons nAMP + dNMPs$$

When the polyribonucleotide segment is not poly A, it is preferred to additionally employ elevated temperatures (45°-60° C.) during the digesting step, thus rendering the polyribonucleotide partially or totally denatured (with respect to its internal base pairing).

The nucleoside phosphates produced in the digesting step (d) are then generally converted to a signal-producing entity (normally ATP). In the case of poly A as the polyribonucleotide segment, all of the ADP or AMP produced in the digestion step has the potential of being converted to ATP; in the case of heterogeneous polyribonucleotide segments, generally only the ADP's or AMP's can produce ATP. Utilization of the other nucleoside phosphates will normally not be made.

Conversion of AMP to ADP can be accomplished with myokinase and a nucleoside triphosphate other than riboadenosine triphosphate, e.g., rCTP, rGTP or rITP. This reaction $$AMP + NTP \rightleftharpoons ADP + NDP$$

is freely reversible and, therefore, is preferably coupled with the subsequent step of converting ADP to ATP.

Conversion of ADP to ATP usually involves a kinase (such as pyruvic acid kinase or PK) and an organophosphate reagent (e.g., phosphoenolpyruvic acid). The reaction catalyzed by this reaction is irreversible:

$$HOOC\text{-}C(=CH_2)\text{-}OPO_3H_2 + ADP \xrightarrow{PK}$$

$$CH_3C(=O)COOH + ATP$$

Enzymes that will similarly convert ADP to ATP (in the presence of appropriate organophosphate reagents) include creatine phosphokinase (CPK, E.C. 2.7.3.2) used with excess creatine phosphate. The same reaction scheme is commonly used to assay for CPK. See U.S. Pat. No. 4,286,057 to Wulff et al. Exemplary references for such enzymes, showing appropriate reaction conditions, include W. D. McElroy and M. A. DeLuco, J. Appl Biochem., vol. 5, pp. 197–209 (1983).

In some preferred forms of the present invention (and in copending application No. 82-2432) the enzymes and reactants for the digesting step (if it produces ADP) and for the phosphorylating step are present together, either because of being introduced as a single stored reagent or by being introduced as separate reagents so as to contact the displaced labeled polynucleotide together. Using polynucleotide phosphorylase (PNP), creatine phosphokinase (CPK) and creatine phosphate (CP) as exemplary, the overall reaction scheme can be:

wherein inorganic phosphate and creatine phosphate (CP) are provided in excess. So long as creatine (Cr) does not build up to an unacceptable degree, the CPK-catalyzed second step will be essentially irreversible, driving the first step in the forward direction as well. Normal cofactors and conditions for the analogous PK reaction include Tris-HCl (pH 8.5), 2-mercaptoethanol (1 mM), pyruvate kinase (PK) (0.4 units/ml), phosphate (0.1M) and phosphoenol pyruvate (PEP) (4.1 mg/ml).

Once ATP is produced by the above steps (either from ADP or from AMP) in an amplified amount functionally related to the amount of displaced labeled polynucleotide, the ATP may be detected in a number of ways, many of which are conventional for the detection of ATP. Exemplary is the luciferin/luciferase method desired in various references including U.S. Pat. Nos. 3,933,592 to Clendenning and 3,423,290 to Seamans (Chappelle) (1969) and the above-cited chapter of The Enzymes, vol. XV. The detection of the emitted light generally is conducted in a luminometer or other light-detector such as an LKB Wallac Company Model 1250 luminometer.

Preferred reagents and conditions for the bioluminescent ATP-detecting step include those described in LKB's U.S. Pat. Nos. 4,235,961 to Lundin (1980) and 4,246,340 to Lundin et al. (1981). In Examples 1 and 2, below, an LKB instrument and LKB reagents were used after the completion of the digestion and phosphorylation steps (run together). As indicated in the above LKB patents, the bioluminescent reaction can be controlled (especially with L-luciferin analogs and pyrophosphate) to produce a level signal over one minute while a reading is being taken. Because it is frequently desired that such one minute follow at a known interval initiation of the bioluminescent reaction, it is preferred that one or both of luciferase and luciferin not be introduced into the reaction mixture until such known interval before detection (e.g., introduced separately into the luminometer instrument).

Numerous other schemes for detecting ATP (with AMP as the byproduct) are known. They include several cited or discussed in U.S. Pat. No. 4,446,231 to Self (1984), the relevant disclosure of which is incorporated by reference. The byproduct of such reactions is AMP, in an amount corresponding on a molar basis both to the ATP consumed and to the photons emitted.

If further amplification is desired, an enzyme such as myokinase may be present (during the detecting step) which catalyzes the reaction:

$$ATP + AMP \rightarrow 2ADP$$

To complete the recycle, however, it would be necessary that the phosphorylating enzyme and its organophosphate reagent (e.g., CPK and CP) also be present during the read-out and that conditions suitable for all steps of the recycle be maintained in the detection site (luminometer chamber) and that detection occur over sufficient time periods for recycle. Furthermore, when myokinase is employed, the various enzymes and reagents introduced must be free of undesired contaminents (e.g., AMP, ADP or ATP) and undesired activities (e.g., catalyzing the hydrolysis of ATP, ADP or of the organophosphate).

Still other ATP-detecting schemes do not produce AMP as the byproduct. They include reactions which release ADP as the byproduct such as the NAD-linked reactions using 3-phosphoglycerol kinase and glyceraldehyde-3-phosphate dehydrogenase.

The ADP produced in the digestion step (d) may also be detected by reaction with phosphoenol pyruvate in the presence of pyruvate kinase, lactate dehydrogenase and either NADH or NADPH. In such case, the first reaction is again:

$$PEP + ADP \rightarrow pyruvate + ATP$$

Now, however, instead of (or in addition to) detecting reaction can occur: the ATP, the following LDH-catalyzed reaction can occur:

$$NADH + pyruvate \rightarrow NAD + lactate$$

By monitoring the rate of disappearance of NADH (e.g., by absorbance at 340 nm), a value can be obtained functionally related to the ADP produced in the digestion step. Other means for detecting the pyruvate (e.g., reaction with DNP-hydrazine) may be used. Furthermore, by having present reactants and enzymes which consume ATP (e.g., fructose-6-phosphate (F6P) and phosphofructose kinase (PFK)), each ADP produced by the digestion step can be recycled as follows:

The above is analogous to col. 8 of U.S. Pat. No. 4,446,231 to Self. The above amplification scheme can be accelerated if the pyruvate kinase used is activated by fructose-1,6-diphosphate (FDP). It should be emphasized that, in such schemes, the ADP is provided (by the digestion step) in limited amounts and the pyruvate is being detected (by LDH-catalyzed oxidation of NADH or otherwise).

Other direct or indirect assays for the AMP or ADP produced directly by the digestion step, or for the ATP produced directly or indirectly from such AMP or ADP are described or can be ascertained from the following U.S. Pat. Nos.:
  4,331,762 to Nakajuma et al. (1982)
  4,338,395 to Leon et al. (1982)
  4,352,881 to Inagawa et al. (1982)
  4,357,420 to Bostick et al. (1982)
  4,368,261 to Klase et al. (1983)
  4,371,611 to Fusee et al. (1983)
  4,394,445 to Nix et al. (1983)
  4,415,655 to de Castro et al. (1983)
  4,438,124 to Meister et al. (1984)
  4,445,594 to Buckmann (1984)
  4,485,177 to Siedel et al. (1984).

The above patents also include additional information and details about methods for detecting AMP, ADP or ATP, discussed above, and especially about methods involving pyruvate kinase and lactate dehydrogenase.

Additionally, the ADP produced in the digestion step may be determined directly by chromatography such as HPLC or fast protein chromatography (using Pharmacia's FPLC instrument). See G. A. Orr et al., *Analytical Biochem.*, vol. 142, pp. 232-234 (1984); V. Stocchi et al., *Anal. Biochem.*, vol. 146, pp. 118-124 (1985).

In the cases in which the signal strand polynucleotide (signal strand) contains a DNA pairing region and an RNA (especially poly A) polyribonucleotide segment, the preferred geometry is DNA at the 5' end and RNA at the 3' end. To produce such signal strands one may start with a DNA polynucleotide and add one or a few ribonucleotides (especially A's) at the 3' end. Terminal deoxynucleotidyl tranferase (TdT) will perform this step in the absence of deoxynucleoside triphoshates and the presence of excess ATP:

TDT

Reaction then with excess ADP and polynucleotide phosphorylase (PNP) (in the absence of significant inorganic phosphate concentrations) will lead to elongation of the rA:

The strand so produced, after removing free ATP and ADP and any unprimed poly A, is now ready for hybridization to produce the reagent complex.

In addition, provided that the 3' end of the probe strand is not in the free 3' hydroxy form (e.g., attached to a substrate, is chemically modified or is otherwise blocked), one may start with either a DNA/DNA hybrid or a DNA-3'-rA/DNA hybrid and elongate with PNP to produce the reagent complex.

Figure 1A:
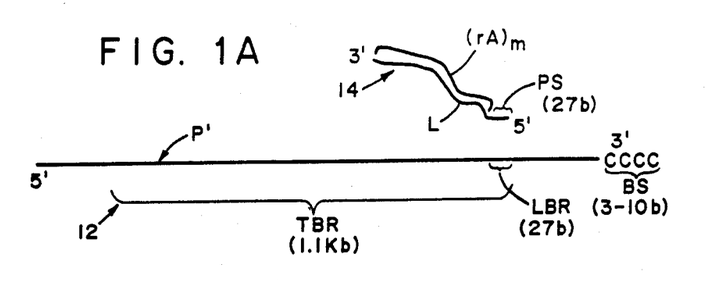

FIG. 1A illustrates a probe polynucleotide 12 or P' and a signal strand polynucleotide 14 or L used to form an embodiment of the reagent complex of the present invention. The probe polynucleotide 12 or P' contains a length of DNA in which an intermediate portion TBR is the target binding region capable of Complementary Base Pair Binding to the target nucleotide sequence sought to be detected. A subsegment of the portion TBR, illustrated at the last 27 nucleotides of TBR in the 3' direction, is the labeled or signal-strand binding region LBR. At the 3' end of the probe polynucleotide 12 is a binding segment BS consisting of 10 or more deoxycytosine nucleotides.

Also illustrated in FIG. 1A is the signal strand polynucleotide L or 14 containing at its 5' end a DNA segment PS (the pairing segment) complementary to the labeled or signal-strand binding region LBR of the probe polynucleotide 12. The remainder of the signal-strand polynucleotide L is a ribopolynucleotide segment illustrated a poly(riboadenosine) segment $(rA)_n$ of length n. As illustrated in Example 1, such a DNA-RNA block copolymer strand can be created efficiently from the 27-mer DNA by addition of adenosine nucleotides in two steps: a priming step with ATP and TdT, and an elongation step with ADP and PNP.

Figure 1B:
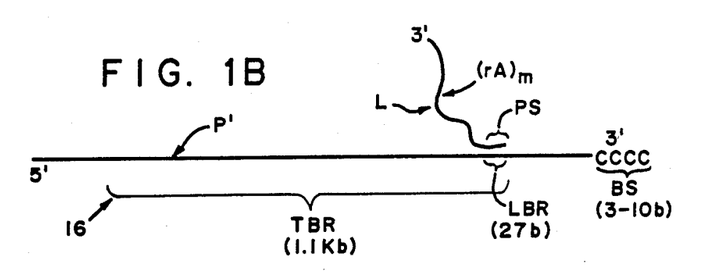

A reagent complex 16 according to the present invention is illustrated in FIG. 1B. It can be prepared by hybridization of the free probe polynucleotide 12 and free signal-strand polynucleotide 14 of FIG. 1A (after suitable purification of each). In reagent complex 16, the pairing segment PS of signal strand polynucleotide L is bound by Complementary Base Pairing to the signal-strand polynucleotide binding region LBR of probe polynucleotide P'. The ribonucleotide segment $(rA)p_n$, including the free 3' end of the signal strand polynucleotide L, is in single-stranded form.

Figure 1C:
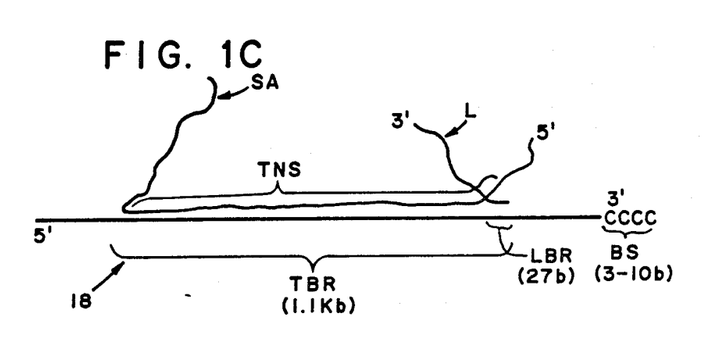
Figure 1D:
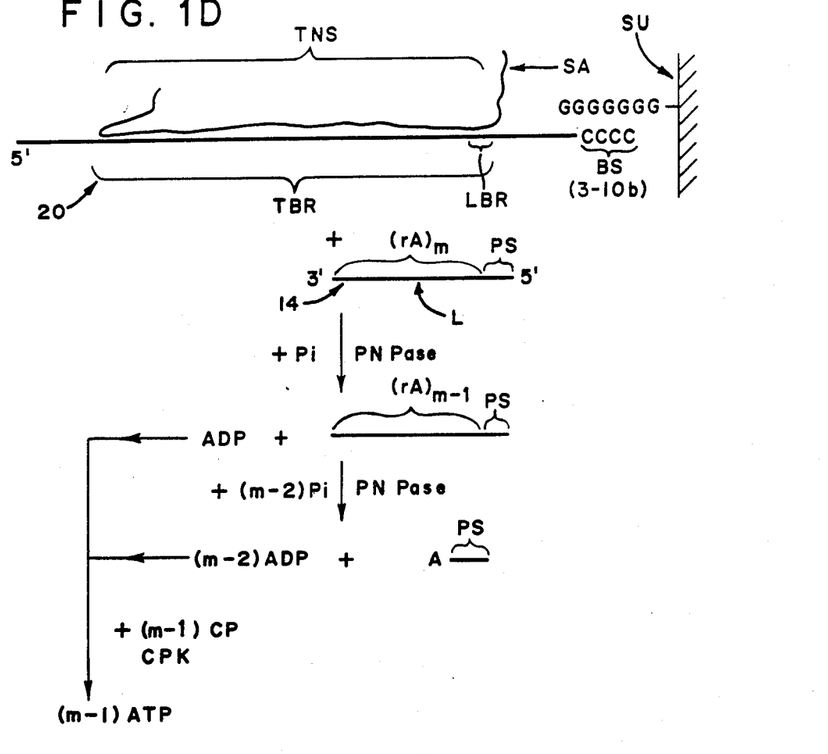

FIG. 1C illustrates the reagent complex of FIG. 1B onto which a sample polynucleotide SA containing the target nucleotide sequence TNS has begun hybridizing. In this intermediate structure 20, most of the target nucleotide sequence TNS has hybridized to corresponding nucleotides of the target binding region TBR of probe polynucleotide P'. The signal strand polynucleotide L remains hybridized, however, to the signal-strand polynucleotide binding region LBR of the probe P'. As described in U.S. Ser. No. 607,885, strand migration can now occur and will result rapidly in displacement of the signal strand polynucleotide L from the probe polynucleotide P'. Furthermore, the reaction mixture may then be subjected to affinity chromtography with an immobilized affinity reagent (e.g., oligo-dG-cellulose) for the binding segment BS of probe P' (the 3-10 base 3'-oligo-dC tail of probe P'). The combination of these two steps (for those reagent complexes which have bound sample SA and displaced signal strand polynucleotide L) is shown in FIG. 1D. Here, the entire target nucleotide sequence TNS of sample polynucleotide SA is hybridized to target binding region TBR of probe P'. These complexes are bound at the binding segment BS to the support SU, on which an affinity reagent (oligo-dG) is immobilized. Also bound to oligo-dG moieties elsewhere on the support SU will be all of the reagent complexes 16 (see FIG. 1B) which still contains signal strand polynucleotide L. The only signal strand polynucleotides L in solution (in the absence of non-specific dissociation and assuming complete capture of reagent complexes 11 by the oligo-dG column) will be those free signal strand polynucleotides 14 resulting from a displacement event.

After the displaced labeled polynucleotide 14 is separated from the solid phase, it is digested with the enzyme polynucleotide phosphorylase (PNP) in the presence of excess inorganic phosphate. This process is illustrated in FIG. 1D in two stages, the cleaving of the first adenosine nucleotide to ADP at the 3' end (to leave n−1 adenosine nucleotides) and then the cleavage of the next (n−2) adenosine nucleotides to form (n-2) ADPs. Because PNP is processive, it will cleave the ribonucleotides processively from the 3' end, leaving a single (or relatively few) ribonucleotides (illustrated as a single A on the deoxynucleotide oligomer PS).

The further action of the phosphorylating enzyme creatine phosphokinase (CPK) is illustrated in the lower portion of FIG. 1D. This enzyme performs the same function as is described in the text and Examples for pyruvate kinase. Thus, all of the ADPs are reacted with excess creatine phosphate (CP) (n−1 are consumed) to form (n−1) ATPs. While the reaction will not necessarily go this far to completion (i.e., all but one of the adenosine nucleotides of signal strand polynucleotide 14 going to ATP), the reaction can be driven to nearly this stage by coupling the two enzymatic reactions together as described in the text.

In similar fashion, if a phosphodiesterase is used for the digestion step, then reagents to produce ATP (from AMP) can be used: myokinase, GTP, phosphoenol pyruvate, pyruvate kinase.

Completing the present method, the ATPs produced are detected, e.g., with luciferin and luciferese in a luminometer. Provided that the sample and various reagents are free of exogenous RNA, ADP and ATP, that non-specific dissociation does not occur, and that the capture of intact reagent complexes 16 by the oligo-dG cellulose column is complete, the light detected will result solely from displacement events. To the extent that these factors are not absolute, some background values of light will appear and (provided that they do not exceed expected levels) can be measured with negative controls and subtracted out in computing amounts of target nucleotide sequence TNS determined.

Figure 2:
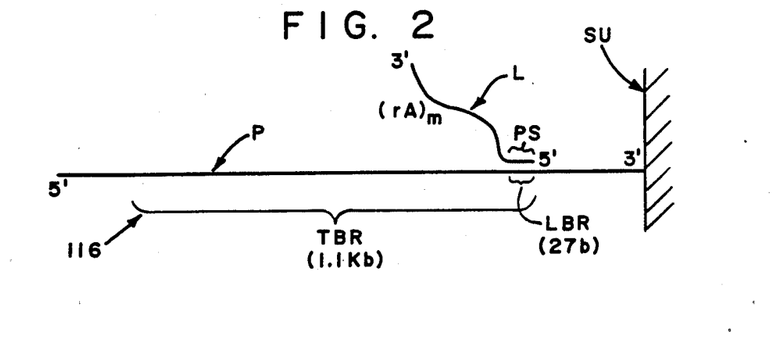

An immobilized reagent complex 116 according to the present invention is illustrated in FIG. 2. In this case the probe P contains a target binding region TBR including a signal-strand polynucleotide binding region LBR and is bound chemically at its 3' end to a support SU. As in FIG. 1B, the signal-strand polynucleotide L contains at its 5' end a DNA pairing reagent complementary and bound to the signal-strand polynucleotide binding region LBR. The signal-strand polynucleotide L also contains, in the middle and at the 3' end, a polynucleotide segment $(rA)_n$.

Use of the reagent complex 116 of FIG. 2 is analogous to the method described above in reference to FIGS. 1C and 1D. Upon contact with sample containing target nucleotide sequences, signal strand polynucleotides L will be displaced into solution. After a simple separation, liquid phase is contacted with phosphate, PNP, CPK and creatine phosphate (CP), whereby displaced signal strand polynucleotides are digested processively to ADP and phosphorylated to ATP. Detection (with luciferin/luciferase) will produce a light measurement functionally related to the number of target nucleotide sequences (TNS) in the sample, with an amplification effect approaching the value of n.

EXAMPLE 1

Preparation of Polyadenylated DNA 100 pmol of the synthetic deoxyoligonucleotide 3'-CTAGTACCGCTGGTGTGGGCAGGACAC-5' was phosphorylated at its 5' terminus with [$^{32}$P] using T4 polynucleotide kinase and γ-[$^{32}$P]ATP. The phosphorylated product, 5'-[$^{32}$P]-PM27, was subsequently purified by ion exchange chromatography using DE-52 cellulose(Watman).

10 pmol of the 5'-[$^{32}$P]PM27 was concentrated by ethanol-sodium acetate precipitation. Following centrifugation, the DNA pellet was redissolved in 12 ul distilled deionized water. To this solution was added 2 ul of terminal deoxynucleotydyl transferase buffer, 2 ul of 20 mM adenosine triphosphate and 4 ul of terminal deoxynucleotidyl transferase (17,000 units/ml). The reaction was allowed to proceed for 60 minutes at 37° C.

The riboadenylated product, 5'-[$^{32}$P]-PM27rA was concentrated by ethanol-sodium acetate precipitation, and following centrifugation, the DNA was redissolved in 12 ul distilled deionized diethylpyrocarbonte (DEPC) treated water. To this solution was added 2 ul of 1M Tris HCl (pH=8.5), 0.01M 2-mercaptoethanol buffer, 3 ul of 25 mM adenosine diphosphate(ADP), 1 ul of polynucleotide phosphorylase and 1 ul of 0.1M MgCl$_2$. The reaction was allowed to proceed for 30 minutes at a temperature of 37° C. The polyadenylate tailed 5'-[$^{32P}$P]-PM27(rA)n (n=number of adenylate residues: approximately 6000 to 8000) was purified by ethanolsodium acetate precipitation and gel filtration on a 1 ml Sephadex G-75 matrix.

Preparation of Reagent Complex 1 pmol of 5'-[$^{32}$P]-PM27(rA)$_n$ was combined with an equimolar (based on PM27-complementary sequences) amount of Hinfl linearized, oligo dC-tailed M13mp9-5/5 DNA (whose precisely described in Ser. No. 729,501 filed May 2, 1985, of P. D. Unger et al., copending, filed herewith, and consists of 205 nucleotides of M13 origin at the 5' end, a 1.1 kb pBR322 insert, 348 nucleotides of M13 origin and 10 or more deoxycytidine residues at the 3' end). The two species were coprecipitated with ethanol and sodium acetate. Following centrifugation the pellet was redissolved in 18 μl distilled deionized DEPC treated sterile water. Following incubation of this solution at 80° C. for 2 minutes, 2 μl of 2M sodium chloride 0.5M-Tris borate buffer (8.0) was added. After an additional 2 minutes at 80° C. the solution was allowed to cool slowly to room temperature for approximately 2 hours.

The volume of the hybrid solution was adjusted to 250 μwith 0.2M NaCl/1xTE and applied to the surface of a 1 ml oligodeoxyguanosine-cellulose column equilibrated in 0.2M NaCl/1×TE buffer. Following a period of 30 minutes at 25° C. for column hybridization, the unhybridized PM27rAn was eluted with 0.2M NaCl/1×TE-buffer. After a subsequent wash with 0.1M NaCl/1×TE buffer, the hybrid species (reagent complex) was eluted with 1×TE buffer. Reagent complex was isolated from this solution by centrifugation following the addition of 3 volumes of ethanol. The reagent complex contains the 27 deoxyribonucleotide residues of PM27(rA)$_n$ bound to the 27 deoxynucleotide residues at the 3' end of the 1.1 kb pBR322 insert in oligo dC-tailed M13mp 9-5/5 DNA. (See Fig. 1B)

Displacement 0.3 pmol of reagent complex was incubated with 0.3 pmol of M13mp8-1/6 competitor DNA (containing 1.1 kilobases complementary to the 1.1 kb pBR322 insert in oligo dC-tailed M13mp9-5/5 DNA) or 0.3 pmol of lambda DNA (non-specific DNA control) in a total volume of 20 μl 1 0.2M NaCl and 1×TE buffer. The samples were annealed at 50° C. for 30 minutes. Both samples were brought to a volume of 250 μl with 0.2M NaCl in 1×TE and bound and free PM27(rA)n species were separated by oligo-dG cellulose chromatography by the same procedures employed above to purify the reagent complex from the hybrid solution.

Detection

To 1 μl aliquots from each oligo dG cellulose fraction (from the displacement step and various controls) to be assayed for the presence of poly A tailed DNA, was added 19 μl of the solution containing 0.05M tris HCl (pH8.5), 0.001M 2-mercaptoethanol, 0.01M $MgCl_2$, 0.01M sodium phosphate, 14 units of polynucleotide phosphorylase, 0.4 units/ml of pyruvate kinase and 0.4 mg/ml phosphoenol pyruvate. The reactions were allowed to proceed at 37° C. for 30 minutes. The volume of the reaction was adjusted to 250 μl and the amount of ATP present was quantitated by a standard LKB bioluminescense assay (employing luciferin and firefly luciferase). The results indicated a detectable increase in the bioluminescent signal for the 0.2MNaCl, 1×TE eluant for samples with appropriate (homologous) competitor compared to control samples with non-homologous (bacteriophage lambda) DNA. Scintillation counting of eluant fractions from the oligo dG cellulose column similarly showed a detectable increase in the 0.2M NaCl, 1×TE eluant for samples with homologous competitor compared to values for control samples.

EXAMPLE 2

PM27 oligomer was labelled at the 5' terminus with $\gamma[^{32}P]ATP$, as described above, to a specific activity of $2.56\times10^5$ cpm/pmol. This reagent was purified by DE-52 anion exchange chromatography. $5'-[^{32}P]PM27$ DNA was quantitatively riboadenylated at the 3' terminus using terminal deoxynucleotidyl transferase in a reaction volume of 20 uL containing 60 pmol of $5'-[^{32}P]$-PM27, 40 nmoles of ATP, 30 units of terminal transferase, 100 mM potassium cacodylate buffer (pH 7.2), 2 mM $CoCl_2$ and 0.2 mM dithiothreitol. Following an incubation period of 40 minutes at 37° C., an additional 30 units of TDT was added. After 20 minutes at 37° C., the reaction was terminated by phenol/chloroform-/isoamyl alcohol extraction (25:24:1, v/v). The riboadenylated deoxyoligomer was collected by ethanol precipitation, the pellet rinsed with ethanol, dried and redissolved in water to a final concentration of 1 pmol/ul based on radioacititvty.

Polyadenylation of $5'[^{32}P]PM27rA1,2$

One pmol of the riboadenylated 27mer was polyadenylated in a reaction mixture containing 100 nmol ADP, 5 mM $MgCl_2$, 50 mM Tris-HCl (pH 8.5), 1 mM 2-mercaptoethanol and 0.14 units of primer dependent polynucleotide phosphorylase from *M. leuteus* (PL Biochemicals) in a final volume of 20 ul. Following incubation for 30 minutes at 37° C., the polyadenylated 27mer (PM27rAn) was extracted and collected as described above for the riboadenylated 27mer. The degree of polymerization was judged by agarose gel electrophoresis to be between 6000 and 8000 adenylate residues using an 8 Kb single stranded DNA as a molecular weight reference. Bioluminescense calibration curves were generated using 0-2 pmoles of PM27rAn (based on radioactivity) following conversion of the polyA tract to ATP. In that curve, 1 pmol of PM27rAn corresponds to 256,000 counts. 0-2 pmoles of PM27rAn were incubated in the presence of 20 mM inorganic phosphate, 5 mM $MgCl_2$, 50 mM Tris-HCl (pH 8.5) 1 mM 2-mercaptoethanol, 7 units of polynucleotide phosphorylase, 0.8 mg/ml phosphoenolpyruvate and 0.008 units of pyruvate kinase in a final volume of 20 ul. Following a 60 minute incubation at 37° C. the reaction volume was adjusted to 250 ul with water and the ATP determined by a standard bioluminescence assay. 250 ul of a standard LKB bioluminescence reagent (see LKB's U.S. Pat. No. ,235,961 and 4,246,340) were added to the digestion mixture. Following a delay period of 180 seconds the bioluminscence was measured for a period of 60 seconds. The bioluminescence measure during this period was found to be proportional to the pmoles of DNA (PM27rAn) present as determined by Cerenkov counting giving a lower limit of sensitivity of 100–200 atomoles of PM27.

Bioluminescent Measurement of an Analyte DNA

Ten pmoles of PM27rAn were annealed to an equal number of pmoles of deoxycytidylate tailed hinfl cut DNA (M13mp19 3/2). The hybrid reagent molecule was purified from unbound PM27rAn by chromatography on a 100 mg column of oligo dG cellulose. The hybridization reaction of volume 20 ul containing 0.2M NaCl and 1×Tris-EDTA buffer was applied to the oligo dG cellulose column and the C-tailed probe DNA molecules allowed to anneal for 30' at 41° C. Unhybridized PM27rAn, ADP and contaminating denovo synthesized polyA tracts (if present) were removed by 3×100 ul washes of 0.2M NaCl buffered with 1×TE buffer.

The hybrid reagent was removed by elution with 3×100 ul volumes of 1×TE in the absence of salt. These fractions were immediately placed on ice and the ionic strength adjusted to 0.4M with 1 tenth volume of 4M NaCl. This hybrid reagent was concentrated by centrifugation. Following precipitation with ethanol, the hybrid reagent was dissolved in 60 ul of 0.4M NaCl 1×TE. Probe strand (about 20% of which was hybridized to Pm27rAn) (1 pmol) was challenged with 0-1 mol of competitor complimentary DNA (M13mp18 20C-1) per pmol probe strand in a final volume of 10 ul and ionic strength of 0.2M NaCl 1×TE. Following incubation at 50° C. for 60 minutes, the reactions were delivered to the surface of 25 mg oligo dG cellulose columns. The C-tailed species (hybrid and probe strands) were allowed to anneal to the column for 30 minutes at 4° C. Displaced signal molecules (PM27rAn) were collected by centrifugation of 250 ul of 0.2M NaCl 1×TE solution through the column. Non-displaced hybrid molecules and probe strands were subsequently collected by centrifugation of a 250 ul volume of distilled water through the column. The PM27rAn present in each fraction was quantitated by Cerenkov counting. The results are shown in Table I. To each 250 ul 0.2M NaCl oligo dG cellulose fraction containing displaced signal strand was added an equal volume of a 2× concentrated polyadenylate phosphorolysis/ATP generating reagent giving final concentrations of the phosphorolysis and phosphorylating reagent indicated in this Example for the generation of the curve. Following conversion of the polyadenylate tract to ATP, the latter was quantitated by bioluminescence as described above except that 500 ul of LKB reagent was used instead of 250 ul. The results are shown in Table I.

The mV values represent bioluminescence read-out resulting from the 0.2M salt and water fractions from each tube. The precise ratios of mV (between column fractions) for each tube are not significant without correction factors because the salt concentration affects one or more of the enzymatic activities and especially the luciferase activity. The trend, however, for the same fraction from tube to tube is significant. Furthermore, the cpm values are lower than for the standard curve (referred to above) by a factor of four because two half-lives of p$^{32}$ had elapsed since the curve was generated. Accordingly, the 3000 cpm levels in Table I correspond to 64,000 cpm×20% binding of PM27rAn.

TABLE I

| Sample | Oligo dG Cellulose Fraction | Pmol Competitor | Pmol Probe DNA[1] | cpm | % Total cpm | Bioluminescence (mv) |
|---|---|---|---|---|---|---|
| 1 | 0.2 M NaCl | | | 35 | | 310 |
| | H$_2$O | | | 2662 | | 40138 |
| | Total | 0 | 1.0 | 2698 | 1.3 | — |
| 2 | 0.2 M | | | 286 | | 2914 |
| | H$_2$O | | | 2763 | | 33820 |
| | Total | 0.1 | 1.0 | 3050 | 9.4 | — |
| 3 | 0.2 M | | | 599 | | 6214 |
| | H$_2$O | | | 2215 | | 31640 |
| | Total | 0.2 | 1.0 | 2815 | 21.3 | — |
| 4 | 0.2 M | | | 1167 | | 12913 |
| | H$_2$O | | | 1591 | | 18495 |
| | Total | 0.5 | 1.0 | 2758 | 42.3 | — |
| 5 | 0.2 M | | | 2724 | | 26590 |
| | H$_2$O | | | 337 | | 465 |
| | Total | 1.0 | 1.0 | 3061 | 89.0 | — |
| 6 | 0.2 M | | | 2720 | | 27613 |
| | H$_2$O | | | 269 | | 603 |
| | Total | 1.0 | 1.0 | 2989 | 91.4 | — |
| | | | Bkg = 25 cpm | 0.2 M NaCl—RNA | Bkg = 4613 | |
| | | | | H$_2$O—RNA | 5048 | |

[1]Approximately 0.2 pmoles PM27rAn per pmole probe DNA annealed during hybrid formation.

We claim:

1. A diagnostic kit for determining the presence of a predetermined target nucleotide sequence in the nucleic acid of a biological sample comprising:
(a) a reagent complex comprising:
   (i) a probe polynucleotide containing a target binding region capable of complementary base pair binding to the target nucleotide sequence, and
   (ii) a signal strand polynucleotide bound by complementary base pairing to a portion of the target binding region, the signal strand polynucleotide containing a plurality of cleavable adenosine ribonucleotides;
   the target nucleotide sequence being capable of displacing the signal strand polynucleotide from the reagent complex;
(b) separation means for separating displaced signal strand polynucleotides from reagent complexes;
(c) enzymatic means for cleaving separated displaced signal strand polynucleotides and producing riboadenosine phosphate monomers; and
(d) detecting means for detecting riboadenosine phosphate monomers produced by the enzymatic means.

2. The diagnostic kit of claim 1 wherein the signal strand contains a DNA segment bound by complementary base pairing to a portion of the target binding region and a single-stranded RNA portion adjacent the 3' terminus.

3. The diagnostic kit of claim 2 wherein the single-stranded RNA portion comprises a polyriboadenosine segment.

4. The diagnostic kit of claim 1 wherein the signal strand comprises a single-stranded polyribadensine segment adjacent to the 3' terminus.

5. The diagnostic kit of claim 4 wherein the enzymatic means comprises an enzyme capable of cleaving monoribonucleotides from a single-stranded polyribonucleotide.

6. The diagnostic kit in claim 5 wherein the enzyme cleaves processively.

7. The diagnostic kit of claim 6 wherein the enzymatic means produces ribonucleoside diphosphates.

8. The diagnostic kit of claim 7 wherein the enzymatic means is a polynucleotide phosphorylase.

9. The diagnostic kit of claim 8 wherein the polynucleotide phosphorylase is from E. coli or M. Luteus.

10. The diagnostic kit of claim 1 wherein the enzymatic means produces ribonucleoside monophosphates.

11. The diagnostic kit of claim 10 wherein the detecting means (d) comprises:
   (i) myokinase and a nucleoside triphosphate for converting the AMP of the ribonucleotide monophosphates to ADP;
   (ii) an organophosphate and a phosphokinase capable of converting the organophosphate and ADP to ATP and a byproduct; and
   (iii) signal producing means for producing a detectable signal concurrently with an obligate hydrolysis of ATP to an adenosine phosphate.

12. The diagnostic kit of claim 11 wherein the myokinase, nucleoside triphosphate, organophosphate and phosphokinase are packaged together.

13. The diagnostic kit of claim 7 wherein the detecting means (d) comprises:
   (i) phosphorylation means for converting the adenosine phosphate produced by the enzymatic means (c) to adenosine triphosphate (ATP), and
   (ii) signal producing means for producing a detectable signal concurrently with an obligate hydrolysis of ATP to an adenosine phosphate.

14. The diagnostic kit of claim 13 wherein the phosphorylation means comprises an organophosphate and a phosphokinase capable of converting the organophosphate and ADP to ATP and a byproduct.

15. The diagnostic kit of claim 14 wherein the enzymatic means, organophosphate and phosphokinase are packaged together.

16. A method for determining the presence of a predetermined DNA target nucleotide sequence in the nucleic acid of a biological sample which comprises the steps:
- (a) providing a reagent complex of (i) a probe polynucleotide which is capable of base pair binding via hydrogen bonds of purine/pyrimidine bases to the target nucleotide sequence, and (ii) a signal strand polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the target nucleotide sequence, the signal strand polynucleotide containing cleavable riboadenosine nucleotides;
- (b) contacting the reagent complex with a sample under conditions in which the target nucleotide sequence, if present, binds to the probe polynucleotide and displaces signal strand polynucleotide from the complex;
- (c) separating a first phase containing displaced signal strand polynucleotide from a second phase containing reagent complexes;
- (d) digesting the displaced signal strand polynucleotides in the second phase to produce ribonucleoside phosphates including riboadenosine phosphates; and
- (e) detecting the riboadenosine phosphate monomers in the ribonucleoside phosphates.

17. The method of claim 16 wherein the digesting step (d) produces nucleoside diphosphates including riboadenosine diphosphate (ADP).

18. The method of claim 17 wherein the digesting step (d) comprises contacting the first phase with a polynucleotide phosphorylase an inorganic phosphate.

19. The method of claim 18 wherein the detecting step (e) comprises:
(i) phosphorylating the ADP to ATP, and
(ii) detecting the ATP.

20. The method of claim 19 wherein the phosphorylating step (e)(i) and digesting step (d) are performed with the polynucleotide phosphorylase, inorganic phosphate, phosphorylating enzyme and organophosphate co-reactant present together, whereby the ADP as formed is converted to ATP.

21. The method of claim 19 wherein the ATP-detecting step (c) (ii) comprises reacting with luciferin in the presence of luciferase.

22. The method of claim 16 wherein the digesting step (d) produces nucleoside monophosphates including riboadenosine monophosphates (AMP).

23. The method of claim 22 wherein the detecting step (e) comprises:
(i) phosphorylating the AMP to ADP;
(ii) phosphorylating the ADP to ATP; and
(iii) detecting the ATP.

24. The method of claim 23 wherein the AMP-phosphorylating step (e)(i) and ADP-phosphorylating step (e)(ii) comprise reacting the product of the digestion step with myokinase, a nucleoside triphosphate other than ATP, an organophosphate and a phosphorylating enzyme capable of converting ADP and the organophosphate to ATP and a byproduct.

25. A reagent complex for determining the presence of a predetermined DNA target nucleotide sequence in the nucleic acid of a biological sample which comprises:
- (a) a probe polynucleotide which is capable of base pair binding via hydrogen bonds of purine/pyrimidine bases to the target nucleotide sequence, and
- (b) a signal strand polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the target nucleotide sequence, the signal strand polynucleotide containing cleavable riboadenosine nucleotides.

26. The reagent complex of claim 25 wherein the probe polynucleotide is DNA, the signal strand contains a DNA segment bound in the reagent complex by base pair binding to nucleotides of the probe polynucleotide and the signal strand contains at its 3' end a ribonucleotide segment.

27. The reagent complex of claim 26 wherein the ribonucleotide segment is polyriboadenosine.

* * * * *